United States Patent [19]

Weinberger et al.

[11] Patent Number: Plant 7,550

[45] Date of Patent: Jun. 11, 1991

[54] APRICOT CV. SUAPRITWO

[75] Inventors: John H. Weinberger; Timothy P. Sheehan, both of Fresno, Calif.

[73] Assignee: Sun World, Inc., Indio, Calif.

[21] Appl. No.: 493,086

[22] Filed: Mar. 12, 1990

Related U.S. Application Data

[60] Division of Ser. No. 385,767, Jul. 26, 1989, abandoned, which is a continuation of Ser. No. 146,334, Jan. 21, 1988, abandoned.

[51] Int. Cl.[5] ..... A01H 5/00

[52] U.S. Cl. ..... Plt./39

[58] Field of Search ..... Plt./39; 800/200

[56] References Cited

U.S. PATENT DOCUMENTS

P.P. 7,4 9/1933 Yount et al. ..... Plt./39

*Primary Examiner*—James R. Feyrer

*Attorney, Agent, or Firm*—William H. Elliott, Jr.

[57] ABSTRACT

An apricot variety characterized by its ripening fruit, unusually bright red blush of medium to large size. Its good quality with low acidity, and good handling qualities.

1 Drawing Sheet

This application is a divisional application of U.S. patent application Ser. No. 385,767, filed July 26, 1989, now abandoned, which was a continuation application of U.S. patent application Ser. No. 146,334, filed Jan. 21, 1988, now abandoned.

This invention relates to the discovery and asexual propagation of a new variety of hybrid apricot *Prunus armeniaca* cv. Suapritwo. The variety is an earlly seasoned hybrid apricot cultivated for dessert fruit. It was discovered by John H. Weinberger and Timothy P. Sheehan in Fresno, Calif., and has as its seed parent the apricot cv. Anna Belle (unpatented). Its pollen parent is not known as fertilization was accomplished by open pollination of the seed parent.

The new variety cv. Suapritwo may be distinguished from other presently available commercial apricot cultivars by the following combination of characteristics: its early ripening, dessert quality fruit of medium to large size and having an unusually large amount of exterior red color in the form of a bright red blush; its delicately flavored fruit with low acidity; and its relatively firm, slow softening fruit flesh which provides good shipping and handling qualities.

As compared to the Apricot variety Blenheim, fruit of the new variety ripens earlier, is larger, has more external red color, and is less susceptible to pit burn at high temperatures. The new variety maintains these distinguishing characteristics through successive asexual propagations by, for example, dormat budding.

Among the characteristics which distinguish the new variety of apricot tree from its seed parent, Anna Belle, may be noted the following combination of characteristics: the new variety has more external red color; firmer, slower softening flesh; and flower buds which require less winter chilling than those of Anna Belle. Consequently, Suapritwo is better adapted to warmer winters and produces a greater quantity of fruit than does Anna Belle.

The pollen parent of the new variety is not known.

The accompanying drawing illustrates, in full color, a typical stem and leaves of the new apricot tree and the ripe fruit as viewed from the stem end and in profile. The drawing also illustrates the fruit sectioned in half from end to end, one-half of the fruit shown with the stone in place in the flesh and the other half shown with the stone removed from the flash.

Throughout this specification, color names beginning with a small letter signify that the name of that color, as used in common speech, is aptly descriptive. Color names with capital letters designate values based upon the Munsell Color Cascade.

Apricots of the new cultivated variety Suapritwo have been deposited before the filing date of this application in an orchard located at 5090 East Church Avenue, Fresno, Calif. and are identified there by applicant's Identification Number 69-165.

The descriptive matter which follows pertains to apricots of the new variety grown in the environment of Fresno, Calif. and is believed to apply to plants of the variety grown under similar conditions of soil and climate elsewhere.

TREE

The tree is of medium size and medium vigor. It is spreading in habit. The foliage density is open. The variety is half-hardy. The trees are medium producers, bearing their fruit regularly. The trees are regular bearers when cross pollinated.

The trunk is of average thickness and the bark average in texture. The branches are average in caliper and are of average smoothness. The branches have a dull surface appearance and carry a average number of average-sized lenticels.

LEAVES

In general, leaves are of medium size, having an average length of about 7½ cm. and an average width of about 5½ cm. Leaves are ovate in outline and up folded in profile. Leaf blade tips curve downwardly at an acute angle. The serrate leaf margin has no undulation. The leaf apex is acuminate; the leaf base is U-shaped. Leaves are of medium thickness.

Leaf color on the upper surface is green in color, near 22-13 Munsell. The upper leaf surface is smooth, with no hairs present and is semi-glossy. The lower leaf surface is green in color, near 22-12 Munsell, weak in glossiness with no hairs present. The lower leaf surface is smooth in texture and has a dull surface appearance.

The petiole is of average length and average thickness. There are usually two medium-sized globose glands positioned alternately on the petiole. Glands are red in color. Stipules are deciduous.

Leaf buds are of average size and conical in shape. Their position, relative to the shoot is slightly held out. Leaf bud supports are decurrent.

Leaf buds burst at an average time for the class.

Anthocyanin coloration, of average intensity, is present in flowering shoots. Shoots are average in thickness for the class. Internode length and bud density is average for the class. Flowering shoots are distributed on spurs and one year old shoots. The ratio of wood (leaf) buds to flowering shoots is 1:2.

FLOWERS

Flower buds are of average size and length for the class. Their shape is plump and positioning is free. Flower bud color is brown near 41-15 Munsell.

Flowers attain full bloom, on the average, around the third week of February which is average as compared with similar varieties growning in Fresno, Calif. Flowers are rosaceous in shape.

FRUIT

The fruit, as now described, was eating ripe. The size of fruit at that stage of its development is uniform, of medium to large size, having an axial diameter of about 5 cm. and a transverse diameter in the suture plane of about 5 cm. Fruit are practically uniform, symmetrical and oblong in shape. The position of the maximum diameter is towards the stem end. The fruit is symmetric about the suture line. Fruit ripens early in season and is for dessert use. Keeping quality of the fruit is good as is the shipping quality.

The suture line is distinct and shallow, extending from the base but is discontinuous at the apex. The ventral surface is rounded, with equal lips. There is no distinct depression of the apex. The pistil base does not persist. Pubescence at the apex is present in an average amount and average density for the class.

The stem cavity is rounded, and usually elongated in the plane of the suture, with the suture show[illegible]n one side. The depth of the stem cavity is about 1.1 cm., and its breadth about 1.3 cm. No markings are present. The base and apex of the fruit are rounded in shape. The pistil point is apical in shape.

The stem is of medium length, about 1½ cm., and adheres weakly to the stone.

The skin, which is of average thickness and of average texture is tenacious to the flesh and shows slight tendency to crack during the dry season. Reticulation and roughness of the skin are absent. Skin color is an apricot yellow near 30-9 Munsell. Down is scant and short and does not roll up when rubbed. There is no bloom.

The color of the flesh is an apricot yellow, near 30-9 Munsell. The amygdalin content of the flesh is wanting and juice is present in moderate amounts. The flesh has an average sugar content. Flesh texture is of medium firmness to melting. Fibers are few and tender. Fruit ripens evenly to produce fruit of good eating quality. The flavor is delicate and the aroma wanting.

The stone is free, adhering to flesh over its ventral edges. The stone retains short fiber-like threads along its ridges. The stone is of medium size, about 3 cm. in length and about 2 cm. in breadth. The width at the stalk end of the stone is about 0.3 cm. and about 1 cm. in thickness. The form of the stone in profile is generally oval and in ventral view is flattened. The stone's base is straight and its apex is rounded. the hilum is narrow. The position of the stone's maximum breadth is toward the middle and the sides are generally equal. The surface of the stone is slightly rough. An outgrowing keel is absent. The ridges are sharply jagged towards the base and apex. The ventral stone edge lacks a wing. The dorsal stone edge is narrow. The stone is near 29-13 Munsell color.

What is claimed is:

1. A new variety of apricot cv. Suapritwo, the variety being particularly distinguished and characterized by its early ripening dessert quality fruit of medium to large size and having an unusually large amount of exterior red color in the form of a bright red blush; its delicately flavored fruit with low acidity; and its relatively firm, slow softening fruit fresh which provides good shipping and handling qualities, essentially as illustrated and described herein.

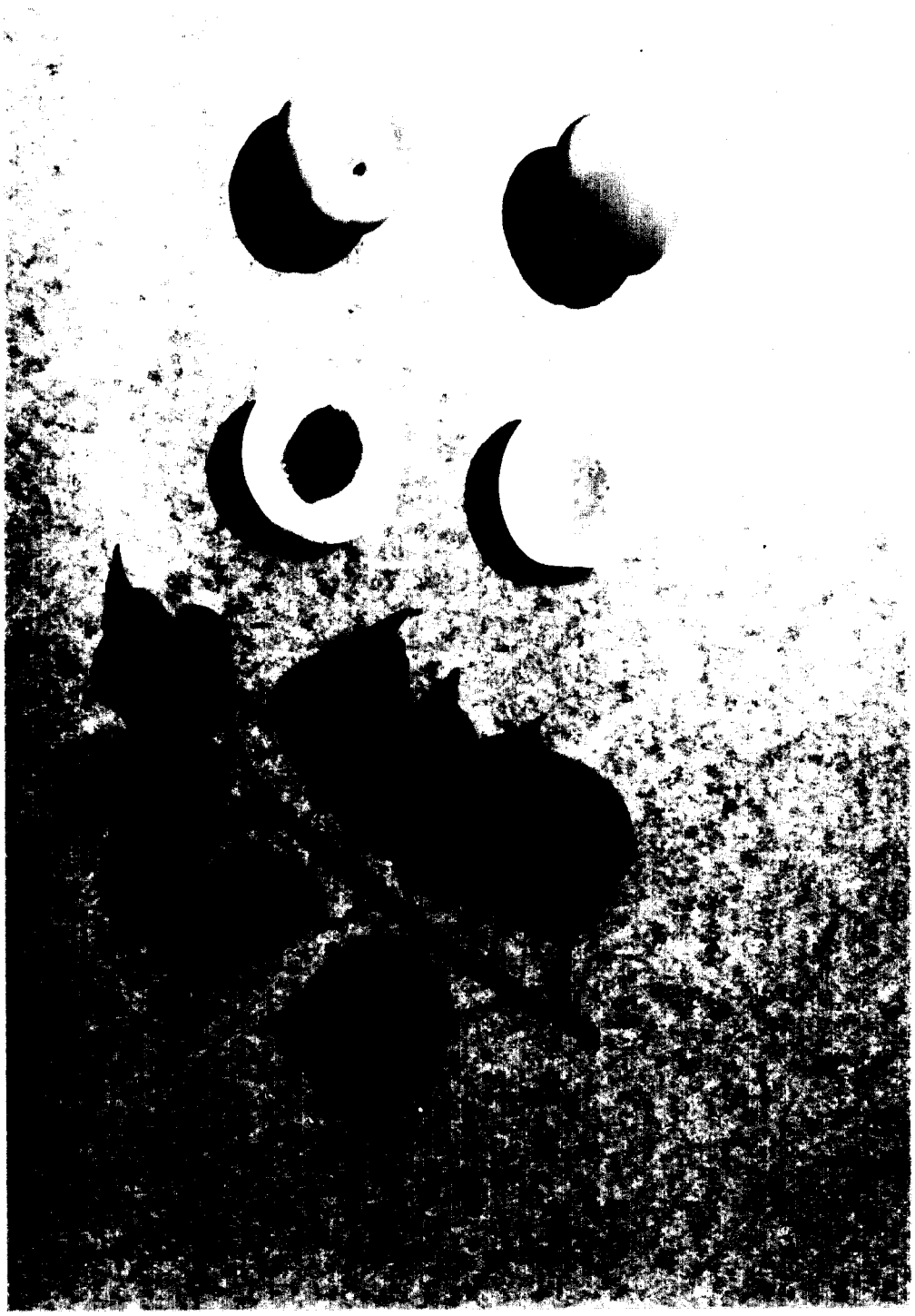

* * * * *